United States Patent
Washburn et al.

(10) Patent No.: US 11,691,933 B2
(45) Date of Patent: Jul. 4, 2023

(54) PROCESSES AND SYSTEMS FOR CONVERTING BENZENE AND/OR TOLUENE VIA METHYLATION

(71) Applicant: ExxonMobil Chemical Patents Inc., Baytown, TX (US)

(72) Inventors: Seth M. Washburn, Houston, TX (US); Hsu Chiang, Humble, TX (US); Catherine M. Dorsi, Houston, TX (US); Tan-Jen Chen, Seattle, WA (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 17/431,846

(22) PCT Filed: Mar. 18, 2020

(86) PCT No.: PCT/US2020/023383
§ 371 (c)(1),
(2) Date: Aug. 18, 2021

(87) PCT Pub. No.: WO2020/197888
PCT Pub. Date: Oct. 1, 2020

(65) Prior Publication Data
US 2022/0153659 A1    May 19, 2022

Related U.S. Application Data

(60) Provisional application No. 62/825,258, filed on Mar. 28, 2019.

(30) Foreign Application Priority Data

Jul. 11, 2019    (EP) ..................... 19185662

(51) Int. Cl.
C07C 2/86      (2006.01)
B01J 8/02      (2006.01)
B01J 29/70     (2006.01)

(52) U.S. Cl.
CPC ............... *C07C 2/865* (2013.01); *B01J 8/02* (2013.01); *B01J 29/7038* (2013.01); *C07C 2/864* (2013.01); *C07C 2529/70* (2013.01)

(58) Field of Classification Search
CPC ..... C07C 2/865; C07C 2/864; C07C 2529/70; B01J 8/02; B01J 29/7038
See application file for complete search history.

(56) References Cited

U.S. PATENT DOCUMENTS 4,587,373 A * 5/1986 Hsia ................... C07C 41/34
                                                 585/408
5,609,734 A * 3/1997 Streicher ............ C07C 7/005
                                                 210/634

(Continued)

FOREIGN PATENT DOCUMENTS

CN    102372585 A    3/2012
WO    1999/38823     8/1999

OTHER PUBLICATIONS

U.S. Appl. No. 17/431,745, filed Aug. 18, 2021 entitled "Processes for Converting Benzene and/or Toluene Via Methylation" Inventors: Seth et al.

(Continued)

*Primary Examiner* — Ali Z Fadhel (57) ABSTRACT

This disclosure provides an improved process for converting benzene/toluene via methylation with methanol/dimethyl ether for producing, e.g., p-xylene, comprising separating and recycling dimethyl ether from the methylation reaction product mixture effluent to the methylation reactor. High selectivity toward p-xylene, among others, can be achieved.

26 Claims, 3 Drawing Sheets

(56) References Cited

U.S. PATENT DOCUMENTS

| | | | |
|---|---|---|---|
| 6,423,879 B1 | 7/2002 | Brown et al. | |
| 6,506,954 B1* | 1/2003 | Brown | C07C 15/08 |
| | | | 585/634 |
| 7,132,580 B1* | 11/2006 | Senetar | C07C 1/20 |
| | | | 208/291 |
| 7,381,676 B1* | 6/2008 | Elia | B01J 29/7088 |
| | | | 502/67 |
| 9,006,506 B2* | 4/2015 | Zheng | C07C 2/865 |
| | | | 585/446 |
| 9,440,893 B2 | 9/2016 | Helton et al. | |
| 9,783,462 B2 | 10/2017 | Ghosh et al. | |
| 9,919,984 B2 | 3/2018 | Ravishankar et al. | |
| 10,647,623 B2* | 5/2020 | Senetar | C07C 1/20 |
| 10,961,168 B2 | 3/2021 | Detjen et al. | |
| 2004/0215043 A1* | 10/2004 | Senetar | C07C 41/34 |
| | | | 585/639 |
| 2013/0253245 A1* | 9/2013 | Zheng | C07C 2/864 |
| | | | 585/467 |
| 2014/0100402 A1* | 4/2014 | Gawlik | C07C 7/005 |
| | | | 585/446 |
| 2016/0060187 A1 | 3/2016 | Kendall et al. | |
| 2018/0099913 A1 | 4/2018 | Chen et al. | |
| 2018/0170828 A1 | 6/2018 | Schmidt et al. | |
| 2018/0170831 A1* | 6/2018 | Jan | C07C 2/864 |
| 2018/0170841 A1 | 6/2018 | Schmidt et al. | |
| 2018/0170842 A1 | 6/2018 | Schmidt et al. | |

OTHER PUBLICATIONS

U.S. Appl. No. 16/820,227, filed Mar. 16, 2020 entitled "Processes for Converting Aromatic Hydrocarbons Using Passivated Reactor" Inventors: Seth et al.

U.S. Appl. No. 17/433,040, filed Aug. 23, 2021 entitled "Processes for Converting Benzene and/or Toluene Via Methylation" Inventors: Seth et al.

* cited by examiner

PROCESSES AND SYSTEMS FOR CONVERTING BENZENE AND/OR TOLUENE VIA METHYLATION

CROSS-REFERENCE TO RELATED APPLICATIONS

This application is a US national phase application of PCT Application Serial No. PCT/US2020/023383 having a filing date of Mar. 18, 2020, which claims priority to and the benefit of U.S. Provisional Application No. 62/825,258 having a filing date of Mar. 28, 2019 and European Patent Application No. 19185662.4 having a filing date of Jul. 11, 2019, the disclosures of all of which are incorporated herein by reference in their entireties.

FIELD

This disclosure relates to processes and systems for converting benzene and/or toluene. In particular, this disclosure relates to processes and systems for converting benzene and/or toluene via methylation with methanol and/or dimethyl ether. This disclosure is useful, e.g., in making p-xylene and/or o-xylene via benzene/toluene methylation with methanol.

BACKGROUND 1,4-Dimethylbenzene (para-xylene, or p-xylene) is a valuable chemical feedstock and is used mainly for the production of terephthalic acid and polyethylene terephthalate resins, in order to provide synthetic textiles, bottles, and plastic materials among other industrial applications. As commercial applications of p-xylene have increased, there has been an increased need for more selective processes and increased yields for p-xylene production. Worldwide production capacity of p-xylene is about 40 million tons per year, and the continually increasing demand for purified terephthalic acid in polyester production processes is projected to provide a corresponding demand to the p-xylene market. Thus, there has been a corresponding increase in demand for the development of efficient and cost-effective p-xylene formation and isolation processes.

p-Xylene can be extracted from the BTX aromatics (benzene, toluene and xylene isomers) in the catalytic reformate produced by catalytic reforming of petroleum naphtha. Alternatively, p-xylene can be produced via toluene disproportionation, toluene transalkylation with C9+ aromatics, or toluene methylation with methanol. Regardless of the method of production, p-xylene is then separated out in a series of distillation, adsorption, crystallization and reaction processes from other C8 aromatic isomers, such as meta-xylene, ortho-xylene, and ethylbenzene. The melting point of p-xylene is the highest among such series of isomers, but simple crystallization does not allow easy purification due to the formation of eutectic mixtures. Consequently, current technologies for p-xylene production are energy intensive, and p-xylene separation and purification are a major cost factor in the production of p-xylene. Hence, alternative methods to selectively produce p-xylene are still needed.

The methylation of toluene or benzene is a favored route to the formation of p-xylene because of the low cost of starting materials and the potential to provide high yields. One methylation method uses methanol as an alkylation reagent. Most of the work related to alkylation with methanol has concentrated on using selectivated zeolite catalysts, such as steamed phosphorous-containing ZSM-5 (U.S. Pat. Nos. 9,440,893B2 and 9,783,462B2) to increase the xylene selectivity to p-xylene. The result of using shape selective catalysts is the need to operate at fairly high temperatures (approx. 500-600° C. or higher), which, in turn, causes rapid catalyst deactivation, significant light gas generation through methanol to olefin chemistry, production of other trace by-products that have to be removed from the product. In the high temperature process, essentially all of the methanol can be consumed.

With the growing need for p-xylene, there is greater demand for cost effective and efficient synthesis and isolation. A challenge that p-xylene manufacturers using conventional technology face is the high cost of catalyst regeneration, high energy consumption, and the need for continued purification processes. In addition, a high selectivity toward p-xylene in the production process is highly desired.

1,2-Dimethylbenzene (ortho-xylene, or o-xylene) is another valuable chemical intermediate, with demand over the past two decades growing at about 2% per year. o-Xylene is used mainly for the production of phthalic anhydride, a common intermediate in production of plasticizers, dyes, and enteric coatings for pharmaceuticals. As commercial applications of o-xylene continue to increase, there is an increased need for more selective processes and increased yields for o-xylene production. The methylation of toluene can also produce o-xylene.

This disclosure satisfies these and other needs.

References for citing in an Information Disclosure Statement ((37 C.F.R. 1.97(h)): U.S. Pub. Nos. 2018/0099913, 2018/0170828, 2018/0170831, 2018/0170841, and 2018/0170842.

SUMMARY

It has been found unexpectedly that in a benzene/toluene methylation with methanol process, by choosing the reaction conditions (including but not limited to hydrocarbon/methylating agent molar ratio and space velocity) such that the methylation reaction mixture effluent comprises both residual methanol and dimethyl ether, the reaction product mixture effluent can comprise p-xylene and o-xylene at near peak concentrations among the xylenes, which are higher than in an equilibrium mixture of p-xylene, o-xylene, and m-xylene. Thus, a high selectivity toward p-xylene and/or o-xylene in the reaction can be achieved. The yield of p-xylene and/or o-xylene can be further enhanced by recycling the methanol and/or dimethyl ether to the methylation reactor.

In a first aspect, this disclosure provides a process for converting benzene and/or toluene, the process comprising: (a) feeding an aromatic hydrocarbon feed and a methylating agent feed into a methylation reactor, wherein the aromatic hydrocarbon feed comprises benzene and/or toluene, and the methylating agent feed comprises methanol and/or dimethyl ether; (b) contacting the aromatic hydrocarbon feed with the methylating agent feed in the presence of a methylation catalyst in the methylation reactor under methylation reaction conditions effective to produce a methylation product mixture effluent exiting the methylation reactor, wherein the methylation catalyst comprises a zeolite of the MWW framework type, and the methylation product mixture effluent comprise toluene, p-xylene, methanol, and dimethyl ether; (c) obtaining a dimethyl ether-rich stream from at least a portion of the methylation product mixture effluent; and (d) recycling at least a portion of the dimethyl ether-rich stream obtained in (c) to (a) as at least a portion of the methylating agent feed.

In a second aspect, this disclosure provides a process for converting benzene and/or toluene, the process comprising: (I) feeding an aromatic hydrocarbon feed and a methylating agent feed into a methylation reactor, wherein the aromatic hydrocarbon feed comprises benzene and/or toluene, and the methylating agent comprises methanol and/or dimethyl ether, wherein the molar ratio of the aromatic hydrocarbon feed to the methylating agent feed is R(a/m), $$R(a/m) = \frac{M(tol) + 2 \cdot M(bz)}{M(\text{methanol}) + 2 \cdot M(DME)},$$

where M(tol) and M(bz) are the moles of toluene and benzene in the aromatic hydrocarbon feed, respectively, and M(methanol) and M(DME) are the moles of methanol and dimethyl ether in the methylating agent feed, respectively, and wherein $1 \leq R(a/m) \leq 5$; (II) contacting the aromatic hydrocarbon feed with the methylating agent feed in the presence of a methylation catalyst in the methylation reactor under methylation reaction conditions effective to produce a methylation product mixture effluent exiting the methylation reactor, wherein the methylation catalyst comprises a zeolite, and the methylation product mixture effluent comprise toluene, p-xylene, methanol, and dimethyl ether; (III) obtaining a dimethyl ether-rich stream from at least a portion of the methylation product mixture effluent; and (IV) recycling at least a portion of the dimethyl ether-rich stream obtained in (c) to (a) as at least a portion of the methylating agent feed.

In a third aspect, this disclosure provides a system for converting benzene and/or toluene to xylenes, comprising: (I) a methylation reactor adapted for receiving a methylation catalyst comprising a zeolite of the MWW framework type comprising at least one reactor inlet adapted for receiving an aromatic hydrocarbon feed and a methylating agent feed and a reactor outlet adapted for discharging a methylation product mixture effluent comprising xylenes, methanol, and dimethyl ether, the methylation reactor further configured to allow contacting the aromatic hydrocarbon feed and the methylating agent feed with the methylation catalyst under methylation reaction conditions effective to produce the methylation product mixture effluent; (II) a separation subsystem in fluid communication with the reactor outlet adapted for obtaining from the methylation product mixture effluent a dimethyl ether-rich stream; and (III) a first recycling channel connecting the separation subsystem and the at least one reactor inlet of the methylation reactor, the first recycling channel adapted for recycling at least a portion of the dimethyl ether-rich stream to the methylation reactor.

DETAILED DESCRIPTION

In this disclosure, a process is described as comprising at least one "step." It should be understood that each step is an action or operation that may be carried out once or multiple times in the process, in a continuous or discontinuous fashion. Unless specified to the contrary or the context clearly indicates otherwise, multiple steps in a process may be conducted sequentially in the order as they are listed, with or without overlapping with one or more other step, or in any other order, as the case may be. In addition, one or more or even all steps may be conducted simultaneously with regard to the same or different batch of material. For example, in a continuous process, while a first step in a process is being conducted with respect to a raw material just fed into the beginning of the process, a second step may be carried out simultaneously with respect to an intermediate material resulting from treating the raw materials fed into the process at an earlier time in the first step. Preferably, the steps are conducted in the order described.

Unless otherwise indicated, all numbers indicating quantities in this disclosure are at to be understood as being modified by the term "about" in all instances. It should also be understood that the numerical values used in the specification and claims constitute specific embodiments. Efforts have been made to ensure the accuracy of the data in the examples. However, it should be understood that any measured data inherently contain a certain level of error due to the limitation of the technique and equipment used for making the measurement.

As used herein, the indefinite article "a" or "an" shall mean "at least one" unless specified to the contrary or the context clearly indicates otherwise. Thus, embodiments using "an ether" include embodiments where one, two or more ethers are used, unless specified to the contrary or the context clearly indicates that only one ether is used.

For the purposes of this disclosure, the nomenclature of elements is pursuant to the version of Periodic Table of Elements as described in CHEMICAL AND ENGINEERING NEWS, 63(5), pg. 27 (1985).

The following abbreviations may be used herein for the sake of brevity: RT is room temperature (and is 23° C. unless otherwise indicated), kPag is kilopascal gauge, psig is pound-force per square inch gauge, psia is pounds per square inch absolute, and WHSV is weight hourly space velocity. Abbreviations for atoms are as given in the periodic table (Li=lithium, for example).

The term "Cn" compound or group, wherein n is a positive integer, means a compound or a group comprising carbon atoms therein at the number of n. Thus, a "Cm to Cn" alkyl means an alkyl group comprising carbon atoms therein at a number in a range from m to n. Thus, a C1-C3 alkyl means methyl, ethyl, n-propyl, or 1-methylethyl-. The term "Cn+" compound or group, wherein n is a positive integer, means a compound or a group comprising carbon atoms therein at the number of equal to or greater than n. The term "Cn-" compound or group, wherein n is a positive integer, means a compound or a group comprising carbon atoms therein at the number of equal to or lower than n.

In the description herein, the catalyst may be described as a catalyst precursor, a pre-catalyst compound, or a catalyst compound, and these terms are used interchangeably.

The term "conversion" refers to the degree to which a given reactant in a particular reaction (e.g., methylation, isomerization, etc.) is converted to products. Thus 100% conversion of toluene to xylene in a methylation refers to complete consumption of the toluene, and 0% conversion of the toluene refers to no measurable reaction of the toluene.

The term "selectivity" refers to the degree to which a particular reaction forms a specific product, rather than another product. For example, for the methylation of toluene, 50% selectivity for p-xylene means that 50% of the products formed are p-xylene, and 100% at selectivity for p-xylene means that 100% of the product formed is p-xylene. The selectivity is based on the product formed, regardless of the conversion of the particular reaction. The selectivity for a given product produced from a given reactant can be defined as weight percent (wt %) of that product relative to the total weight of the products formed from the given reactant in the reaction.

"Alkylation" means a chemical reaction in which an alkyl group is transferred to an aromatic ring as a substitute group thereon from an alkyl group source compound. "Methylation" means alkylation in which the transferred alkyl group is a methyl. Thus, methylation of benzene can produce toluene, xylenes, trimethylbenzenes, and the like; and methylation of toluene can produce xylenes, trimethylbenzenes, and the like. Toluene methylation with methanol in the presence of a zeolite catalyst can be schematically illustrated as follows:

Xylenes    C9

The xylenes include 1,2-dimethylbenzene (ortho-xylene, or o-xylene), 1,3-dimethylbenzene (meta-xylene, or m-xylene), and 1,4-dimethylbenzene (para-xylene, or p-xylene). One or more of these xylene isomers, particularly p-xylene and/or o-xylene, are high-value industrial chemicals. They can be separated to make corresponding products. The C9 hydrocarbons, though, are generally undesirable byproducts. The methylation reaction above can be performed in the presence of a zeolite catalyst.

As used herein, the term "molecular sieve" means a crystalline or semi-crystalline substance, e.g. a zeolite, with pores of molecular dimensions that permit the passage of molecules below a certain size.

In this disclosure, unless specified otherwise or the context clearly indicated otherwise, "space hourly weight velocity" is based on the combined flow rate of the aromatic hydrocarbon feed and the methylating agent feed.

It has been discovered that stable performance can be achieved in toluene methylation with methanol by using MWW zeolite catalysts at lower temperatures (e.g., below 500° C.). The use of the MWW zeolite catalysts at lower temperature can enable the production at exceedingly low quantity of light gas and many of the other by-products which can be generated at much higher quantity in a traditional high-temperature process. Compared to traditional high-temperature processes, this enables significant capital savings as separation and purification of the light gas and other unwanted by-products otherwise generated at high temperature is no longer needed. Furthermore, costs related to catalyst regeneration and energy consumption are decreased at the lower temperature thereby decreasing operation costs. The methylation of toluene at lower temperatures removes issues with light gas generation, lowers energy consumption and catalyst deactivation, but is not selective to the formation of the p-isomer. There is a need to further improve p-xylene and/or o-xylene formation processes by increasing selectivity towards formation of p-xylene and o-xylene thus lowering the costs of isolation of the p-xylene and o-xylene isomers while maintaining the lower costs associated with the lower temperature xylene formation process.

According to this disclosure, it has been found that performing methylation of benzene and/or toluene with methanol in the presence of a zeolite such as a MWW framework type zeolite within certain space time range and at a temperature lower than 500° C., benzene and/or toluene can be alkylated with methanol and/or dimethyl ether to produce a methylation reaction product mixture effluent comprising xylenes with a higher selectivity for p-xylene, and less light gas by-products, with a longer catalyst cycle life, compared to conventional toluene/benzene methylation processes. For example, stopping the methylation process before methanol and dimethyl ether are completely consumed can lead to higher selectivity to p-xylene. The methanol and DME in the methylation product mixture effluent can be separated and recycled to the methylation reactor unit to enhance yield of p-xylene and/or o-xylene. In conventional toluene methylation processes for making p-xylene, the reactant methanol is typically completely consumed in the methylation reactor, leaving very little, if any, of it in the methylation reaction product mixture effluent. It is surprising and counterintuitive to not allow methanol and dimethyl ether to be consumed in their entirety in the methylation reactor.

Methods and apparatuses of this disclosure can provide high selectivity in a low temperature process for producing p-xylene. Applicant has found, unexpectedly, that while the zeolite structures of the MWW framework may have pores that are too large to facilitate shape selectivity of xylene isomers, the initial xylene species formed resulting from methylation reactions are primarily o-xylene and p-xylene, and that m-xylene may be formed primarily through isomerization of the initially formed o- and p-xylenes. Furthermore, in the methylation reactor, it is probable that methanol enters and is converted to and comes to equilibrium with dimethyl ether (DME), then the concentration of methanol and DME declines as the toluene or benzene is alkylated with adsorbed methyl groups. If the reactor is large enough and the reaction allowed to proceed sufficiently, substantially most or all of the methanol and dimethyl ether may be consumed, and the various xylene isomers may isomerize to equilibrium concentrations.

Applicant has found that in order to maintain a high selectivity to p-xylene, one can stop the reaction at the peak of the p-xylene concentration, before much isomerization to meta-xylene has occurred. The peak concentration occurs at lower methanol utilization and therefore methanol and dimethyl ether (DME) would be included in the methylation product mixture effluent leaving the methylation reactor. Therefore, recovery and recycling of the methanol and DME can aid in achieving the high p-xylene selectivity. Stopping the reaction before complete consumption of methanol and DME can be accomplished through higher weight hourly space velocities (WHSVs) as compared to performing the reaction at lower WHSVs which would otherwise consume substantially most or all of the DME and/or methanol.

Methanol can be recovered by first separating aqueous material (aqueous phase) in the methylation product mixture effluent from the oil phase (the aqueous phase carries most of the methanol with it), and then recovering the methanol from the aqueous material. DME can be recovered from the oil phase using distillation. At certain pressures DME may be condensed without the need for cryogenic temperatures in the overhead of the distillation unit while still maintaining a bottoms temperature low enough to minimize thermal induced reactions.

Furthermore, applicant has found that at higher pressures in the methylation reactor, the separation of the alkylation and isomerization reaction waves increases, as the alkylation is a higher order with respect to concentration and increases faster with pressure than the isomerization. Therefore, it is possible to increase p-xylene selectivity by running at higher pressures, as compared to conventional methylation processes, and stopping the reaction at intermediate methanol utilization.

Methylation processes for producing xylenes, such as p-xylene, can be conducted at temperatures ≤500° C. in order to produce xylenes with less light gas by-products and longer catalyst cycle life than high temperature processes. In this disclosure, an aromatic hydrocarbon feed comprising benzene and/or toluene is introduced to a methylating agent feed comprising methanol and/or dimethyl ether in at least one methylation reactor in the presence of a methylation catalyst under methylation reaction conditions, to produce a methylation product mixture effluent, removing a methanol-rich stream and/or a dimethyl ether-rich stream from the methylation product mixture effluent in order to recycle the methanol-rich and dimethyl ether-rich streams to the methylating agent feed, and recovering an aromatics-rich stream comprising p-xylene.

The selectivity to xylenes in a process can be on the order of 80%, with the main by-products being benzene, toluene and C9+ aromatics. The benzene and/or toluene can be separated from the methylation product mixture effluent and recycled to the methylation reactor(s), while the C9+ aromatics can be separated for blending into the gasoline pool or transalkylated with additional benzene and/or toluene to make additional xylenes. The life of the methylation catalyst can be enhanced as compared with existing processes because of the lower methanol decomposition at lower reaction temperatures. Moreover, the use of a larger pore molecular sieve can decrease diffusion limitations and allows the methylation to be carried out at higher WHSVs than allowed with smaller pore molecular sieves.

Methylation Process

The feeds of processes of this disclosure may include an aromatic hydrocarbon feed comprising benzene and/or toluene, and a methylating agent feed comprising one or more of methanol and dimethyl ether. Any suitable refinery aromatic feed can be used as the source of the benzene and/or toluene. In some embodiments, the aromatic hydrocarbon feed comprises toluene at a concentration ≥90 wt % (e.g., ≥92 wt %, ≥94 wt %, ≥95 wt %, ≥96 wt %, ≥98 wt %, or even ≥99 wt %), based on the total weight of the aromatic hydrocarbon feed. In some embodiments, the aromatic hydrocarbon feed may be pre-treated to remove catalyst poisons, such as nitrogen and sulfur-compounds. The aromatic hydrocarbon feed may be fed as a single or multiple streams with the same or different compositions into the methylation reactor via one or more feed inlets. The methylating agent feed may be fed as a single or multiple streams with the same or different compositions into the methylation reactor via one or more feed inlets. Alternatively or additionally, at least a portion of the aromatic feed and at least a portion of the methylating agent feed may be combined and then fed into the methylation reactor as a single or multiple stream via one or more inlets.

A methylation process of this disclosure can be advantageously conducted at relatively low reactor (methylation reactor) temperatures, for example ≤500° C., such as ≤475° C., ≤450° C., ≤425° C., or ≤400° C. A process may be conducted at temperatures of ≥200° C., such as ≥250° C., or ≥300° C. in the methylation reactor which has been found to provide commercially viable methylation reaction rates. In terms of ranges, the process may be conducted at temperatures ranging from 200° C. to 500° C., such as from 275° C. to 475° C., from 300° C. to 450° C., or from 250° C. to 400° C. Such low-temperature reaction can be particularly utilized when a MWW framework type zeolite is present in the methylation catalyst. Such low-temperature reaction can be particularly advantageous where a fixed bed of the methylation catalyst is present in the methylation reactor. The ability of the processes of this disclosure to be operated at low temperature carries many advantages, to name a few: higher energy efficiency, longer catalyst life, fewer species of byproducts, and small quantities of byproducts that otherwise would be produced at higher temperatures, compared to conventional benzene/toluene methylation processes at temperatures higher than 500° C.

Operating pressures in the methylation reactor (in the reactor or methylation reactor) can vary in a broad range, e.g., from ≥100 kPa, such as ≥1000 kPa, ≥1500 kPa, ≥2000 kPa, ≥3000 kPa, or ≥3500 kPa, to ≤8500 kPa, such as ≤7000 kPa, or ≤6000 kPa. For example, operating pressures may range from 700 kPA to 7000 kPa, e.g., from 1000 kPa to 6000 kPa, or from 2000 kPa to 5000 kPa. In at least one embodiment, the combination of a high pressure (e.g., a pressure from 1500 kPa to 4500 kPa or even closer to 8500 kPa) and a low temperature (e.g., a temperature from 250-500° C.), decreases the amount of light gases produced in the methylation reaction, and may also decrease the catalyst aging rate.

WHSV values based on total aromatic hydrocarbon feed and methylating agent feed can be in the range from, e.g., 0.5 hour$^{-1}$ to 50 hour$^{-1}$, such as from 5 hour$^{-1}$ to 15 hour$^{-1}$, from 1 hour$^{-1}$ to 10 hour$^{-1}$, or from 5 hour$^{-1}$ to 10 hour$^{-1}$, or from 6.7 hour$^{-1}$ to 10 hour$^{-1}$. In some embodiments, at least part of the aromatic hydrocarbon feed, the methylating agent feed and/or the methylation product mixture effluent may be present in the methylation reactor in the liquid phase. As is described in more detail below, alteration of the WHSV may be desired in concert with changes in temperature in order to maintain desired conversion of benzene, toluene, methanol, and/or dimethyl ether.

The methylation reaction can be conducted in a methylation reactor, which can be any suitable reactor system comprising, but not limited to, a fixed bed reactor, a moving bed reactor, a fluidized bed reactor, and/or a reactive distillation unit. In addition, the reactor may include a single methylation reaction zone or multiple methylation reaction zones therein. A methylation reactor may include a bed of methylation catalyst particles where the particles have insignificant motion in relation to the bed (a fixed bed). In addition, injection of the methylating agent feed can be effected at a single point in the methylation reactor or at multiple points spaced along the methylation reactor. The aromatic hydrocarbon feed and the methylating agent feed may be premixed before entering the methylation reactor or before entering a methylation reactor within the methylation reactor.

In certain embodiments, the methylation reactor includes a single or a plurality of fixed bed, continuous flow-type reactors in a down flow mode, where the reactors may be arranged in series or parallel. The methylation reactor may include a single or multiple catalyst beds in series and/or in parallel. The methylation catalyst beds may have various configurations such as: a single bed, several horizontal beds, several parallel packed tubes, multiple beds each in its own reactor shell, or multiple beds within a single reactor shell. In certain embodiments the fixed beds provide uniform flow distribution over entire width and length of bed to utilize all of the catalyst. In at least one embodiment, the methylation reactor can provide heat transfer from a fixed bed to provide effective methods for controlling temperature.

The concentration of methylating agent feed can be adjusted by, e.g., staged additions thereof. By staged additions, aromatic hydrocarbon/methylating agent feed concentrations can be maintained at sufficient levels for desirable toluene conversion. In at least one embodiment, the ratio of aromatic hydrocarbon feed to methylating agent feed is R(a/m) which is determined by the following equation:

$$R(a/m) = \frac{M(tol) + 2 \cdot M(bz)}{M(methanol) + 2 \cdot M(DME)}$$

where M(tol) is the moles of toluene in the aromatic hydrocarbon feed, M(bz) is the moles of benzene in the aromatic hydrocarbon feed, M(methanol) is the moles of methanol in the methylating agent feed, and M(DME) is the moles of dimethyl ether in the methylating agent feed. In various embodiments, R(a/m)≥1, or ≥2, or ≥2.5, and ≤6, ≤5, or ≤4, or, e.g., in a range from 1 to 5 or from 2 to 4. For the purpose of producing xylenes, each benzene molecule needs to be methylated by two methanol molecules or one DME molecule, and each toluene by one methanol molecule or half a DME molecule. Over-methylation of benzene and/or toluene can result in the production undesirable C9+ aromatic hydrocarbons as byproducts. To prevent over-methylation, it is highly desirable that R(a/m)≥1.5. Preferably 2≤R(a/m)≤5. More preferably 2≤R(a/m)≤4. The efficiency of the methylation process can be reduced at higher R(a/m), e.g., R(a/m) ≥5, due to large quantity of toluene/benzene present in the methylation reaction product mixture effluent, which needs to be separated and recycled to the methylation reactor.

The efficiency of a methylation reactor containing a fixed bed of methylation catalyst may be affected by the pressure drop across the fixed bed. The pressure drop depends on various factors such as the path length, the methylation catalyst particle size, and pore size. A pressure drop that is too large may cause channelling through the catalyst bed, and poor efficiency. In some embodiments, the methylation reactor has a cylindrical geometry with axial flows through the catalyst bed.

The various designs of the methylation reactor may accommodate control of specific process conditions, e.g., pressure, temperature, and WHSV. The WHSV determines volume and residence time that may provide the desired conversion.

The product of the methylation reaction, the methylation product mixture effluent, can comprise xylenes, benzene and/or toluene (both residual and coproduced in the process), C9+ aromatic hydrocarbons, co-produced water, and unreacted methanol and DME. In some embodiments, p-xylene is present in the methylation product mixture effluent at ≥30 wt %, e.g., ≥40 wt %, ≥50 wt %, or ≥60 wt %, based on the total weight of all xylenes in the methylation product mixture effluent. m-Xylene may be present in the methylation product mixture effluent at ≤30 wt %, e.g., ≤20 wt %, ≤15 wt %, or ≤10 wt %, based on the total weight of all xylenes in the methylation product mixture effluent. In some embodiments, the ratio of a p-xylene to m-xylene (pX:mX) in the methylation product mixture effluent can be greater than 2:1, such as greater than 3:1, greater than 5:1, or greater than 7:1. In some embodiments, the ratio of o-xylene to m-xylene (oX:mX) in the methylation product mixture effluent can be greater than 1:1, such as greater than 2:1, greater than 3:1, or greater than 4:1. In some embodiments, the ratio of a combination of p-xylene and o-xylene to m-xylene (pX+oX:mX) in the methylation product mixture effluent is greater than 2:1, such as greater than 3:1, greater than 5:1, greater than 8:1, or greater than 10:1. In some embodiments, the process is operated at sufficient WHSV so that only a portion of the methanol is reacted with the aromatic hydrocarbon feed and the methylation product mixture effluent contains residual methanol and/or DME.

The temperature in the methylation reactor will affect by-product formation and a temperature lower than 500° C. may decrease light gas formation. In some embodiments, the methylation product mixture effluent contains ≤10 wt %, such as ≤2 wt %, ≤1 wt %, or is substantially free of light gases generated by methanol decomposition to ethylene or other olefins.

DME, methanol, and/or toluene can be recovered through a separation subsystem. The separation subsystem may include one or more separation units. The separation subsystem may include any suitable method for recovery of a DME-rich stream, a methanol-rich stream, and/or a toluene-rich stream from the methylation product mixture effluent. In some embodiments, the separation subsystem includes a first recycle channel. In some embodiments, the first recycle channel is in fluid communication with the methylation agent feed or a methylation reactor inlet. In some embodiments, the separation subsystem includes a first separation unit, the first separation unit may separate an aqueous phase and an oil phase. In some embodiments, the separation subsystem includes a second separation unit, the second separation unit may separate a DME-rich stream from the oil phase. In some embodiments, the DME-rich stream flows through the first recycle channel which may be in fluid communication with the second separation unit and the methylation agent feed or a methylation reactor inlet. In another embodiment the second separation unit separates an aromatics rich stream from the oil phase. In some embodiments, the separation subsystem includes a third separation unit. The third separation unit may separate the aromatics-rich stream into a toluene-rich stream and a xylenes-rich stream. In some embodiments, the toluene-rich stream flows through a second recycle channel to the methylation agent feed or a methylation reactor inlet. In some embodiments, the separation subsystem includes a fourth separation unit, the fourth separation unit may separate the aqueous phase into a water-rich stream and a methanol-rich stream. In at least one embodiment, the methanol-rich stream flows through the third recycle channel which may be in fluid communication with the fourth separation unit and the methylation agent feed or a methylation reactor inlet.

In some embodiments, the methylation product mixture effluent is separated into an aqueous phase and an oil phase in a first separation unit. The method of separating the aqueous phase from the oil phase can be accomplished by a coalescing plate separator, e.g., described in U.S. Pat. Nos. 4,722,800 and 5,068,035; a centrifugal separator, e.g., described in U.S. Pat. Nos. 4,175,040; 4,959,158; and 5,591,340; a hydrocyclone separator, e.g., described in U.S. Pat. Nos. 4,428,839; 4,927,536; and 5,667,686; or other suitable methods. In some embodiments, the oil phase of the methylation product mixture effluent may contain at least 80 wt % xylenes. In some embodiments, the methylation product mixture effluent comprising an aqueous phase and an oil phase enters a first separation unit; the aqueous phase, which is denser, settles to the bottom of an upstream chamber and can be drawn from the water drain tube down below. The oil phase, which is lighter, is located on top of the aqueous phase and can spill over a dividing wall to the downstream chamber where it can then be drawn from the bottom of the downstream chamber.

After separation of the aqueous phase, the oil phase may be fed to a second separation unit to separate a DME-rich stream, an aromatics-rich stream, and methane or other by-products. In some embodiments, the DME-rich stream may be fully or partially separated from other products and by-products to be recycled through the first recycling channel. In some embodiments, the DME-rich stream contains DME in ≥50 wt %, ≥60 wt %, ≥70 wt %, ≥80 wt %, ≥90 wt %, ≥95 wt %, ≥98 wt %, or ≥99 wt %, based on the total weight of the DME-rich stream. In some embodiments, the methylating agent feed contains DME from the DME-rich stream in ≥20 wt %, ≥40 wt %, ≥60 wt %, ≥80 wt %, ≥90 wt %, ≥95 wt %, ≥98 wt %, or ≥99 wt %, based on the total weight of the DME in the methylating agent stream. In at least one embodiment all of the DME in the methylation agent feed is obtained from the DME-rich stream.

In some embodiments, the second separation unit partially or fully separates methane from other products, and by-products. In at least one embodiment, the methane is used as fuel gas.

In some embodiments, the second separation unit produces an aromatics-rich stream comprising C6 to C9+ aromatic hydrocarbon products and by-products. In another embodiment, the second separation unit produces a stream of C9+ aromatics. In at least one embodiment, the stream of C9+ aromatics can be recovered for blending into the gasoline pool or transalkylated with benzene and/or toluene to make additional xylenes. In some embodiments, the second separation unit produces a aromatics-rich stream comprising xylenes in ≥50 wt %, ≥60 wt %, ≥70 wt %, ≥80 wt %, ≥90 wt %, ≥95 wt %, ≥98 wt %, or ≥99 wt %, based on the total weight of the aromatics-rich stream. In some embodiments, the aromatics-rich stream comprises p-xylene. In some embodiments, the aromatics-rich stream contains p-xylene in ≥50 wt %, ≥60 wt %, ≥70 wt %, ≥80 wt %, ≥90 wt %, ≥95 wt %, ≥98 wt %, or ≥99 wt %, based on the total weight of the aromatics-rich stream.

In some embodiments the second separation unit is a distillation system comprising one or more distillation columns. The distillation system may be operated at increased pressure, such as ≥400 kPag, ≥500 kPag, ≥600 kPag, ≥700 kPag, ≥800 kPag, ≥900 kPag, such as from 400 kPag to 1400 kPag, from 600 kPag to 1300 kPag, from 700 kPag to 1200 kPag, from 800 kPag to 1100 kPag, or from 900 kPag to 1000 kPag.

In some embodiments, the aromatics-rich stream is processed in a third separation unit and further separated into a xylenes-rich stream and a toluene-rich stream, which may comprise benzene. The toluene-rich stream comprising benzene and/or toluene (to be recycled through a second recycling channel) may contain toluene in ≥50 wt %, ≥60 wt %, ≥70 wt %, ≥80 wt %, ≥90 wt %, ≥95 wt %, ≥98 wt %, or ≥99 wt %, based on the total weight of the toluene-rich stream. In another embodiment, the toluene-rich stream comprises benzene and toluene in a combined wt % of ≥50 wt %, ≥60 wt %, ≥70 wt %, ≥80 wt %, ≥90 wt %, ≥95 wt %, ≥98 wt %, or ≥99 wt %, based on the total weight of the toluene-rich stream. In some embodiments, the xylenes-rich stream contains an equilibrium mixture of ortho-, meta-, para-xylenes comprising about 24 wt % of p-xylene, about 50 wt % of meta-xylene, and about 26 wt % of ortho-xylene. The xylenes-rich stream may contain p-xylene in ≥10 wt %, ≥20 wt %, ≥30 wt %, ≥40 wt %, ≥50 wt %, ≥60 wt %, ≥70 wt %, or ≥80 wt %, based on the total weight of the xylenes-rich stream.

The xylenes-rich stream and one or more downstream C9+ transalkylation process streams may be sent to xylenes-loop to recover a p-xylene product and an optional o-xylene product. A xylenes loop can comprise a p-xylene recovery unit, such as a crystallization separation unit and/or an adsorptive chromatography separation unit known in the prior art. The p-xylene recovery unit can produce a high-purity p-xylene product and a p-xylene-deleted stream rich in o-xylene and m-xylene. The xylenes-loop can further comprise an isomerization unit such as a vapor-phase isomerization unit and/or a liquid phase isomerization unit known in the prior art to further convert a portion of the o-xylene and m-xylene in the p-xylene-depleted stream to p-xylene. The isomerized stream can be recycled to the p-xylene recovery unit in the xylenes loop to recover additional quantity of p-xylene.

In certain embodiments, the aqueous phase is transferred to a fourth separation unit to separate a methanol-rich stream from a water-rich stream. In some embodiments, the methanol-rich stream to be recycled through the third recycling channel contains methanol at ≥50 wt %, ≥60 wt %, ≥70 wt %, ≥80 wt %, ≥90 wt %, ≥95 wt %, ≥98 wt %, or ≥99 wt %, based the overall weight of the methanol-rich stream. In some embodiments the fourth separation unit is a distillation system, an example system is described in U.S. Pat. Nos. 3,293,154 and 4,210,495. In other embodiments the separation system employed is a membrane separation system or pervaporation separation system.

In another embodiment, the DME-rich stream is combined with the methanol-rich stream to form a single recycle stream. In another embodiment, the toluene-rich stream, the DME-rich stream, and the methanol-rich stream are combined to form a single recycle stream.

Methylation Catalyst

Any suitable catalyst capable of converting toluene (or benzene) to xylenes can be used for the methylation process of this disclosure. Examples of such catalysts are crystalline microporous materials including zeolite-based, as well as non-zeolite-based, molecular sieves and can be of the large, medium, or small pore type. Molecular sieves can have 3-dimensional, four-connected framework structure of corner-sharing [TO$_4$] tetrahedra, where T can be a tetrahedrally coordinated atom. These molecular sieves are often described in terms of the size of the ring that defines a pore, where the size is based on the number of T atoms in the ring. Other framework-type characteristics include the arrangement of rings that form a cage, and, when present, the dimension of channels, and the spaces between the cages. See van Bekkum, et al, Introduction to Zeolite Science and Practice, Second Completely Revised and Expanded Edition, Volume 137, pages 1-67, Elsevier Science, B. V., Amsterdam, Netherlands (2001). Another convenient measure of the extent to which a molecular sieve provides control of molecules of varying sizes to its internal structure is the Constraint Index. The method by which is Constraint Index is determined is described fully in U.S. Pat. No. 4,016,218, which is incorporated herein by reference for details of the method.

Non-limiting examples of molecular sieves include small pore molecular sieves (e.g., AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof), medium pore molecular sieves (e.g., AFO, AEL, EUO, HEU, FER, MEL, MFI, MTW, MTT, TON, and substituted forms thereof), large pore molecular sieves (e.g., EMT, FAU, and substituted forms thereof), intergrowths thereof, and combinations thereof. Other molecular sieves include, but are not limited to, ANA, BEA, CFI, CLO, DON, GIS, LTL, MER, MOR, MWW, SOD, intergrowths thereof, and combinations thereof. In some embodiments, the molecular sieve has an MWW framework type (morphology).

The small, medium, and large pore molecular sieves have from a 4-ring to a 12-ring or greater framework-type. In some embodiments, the zeolitic molecular sieves have 6-, 8-, 10-, or 12-ring structures and an average pore size in the range from about 3 Å to 15 Å. In other embodiments, the molecular sieves are aluminosilicate molecular sieves and have a 6-ring or an 8-ring structure and an average pore size of about 5 Å or less, such as in the range from 3 Å to about 5 Å, for example from 3 Å to about 4.5 Å or from 3.5 Å to about 4.2 Å.

Other non-limiting examples of zeolitic and non-zeolitic molecular sieves include one or a combination of the following: Beta (U.S. Pat. No. 3,308,069 and Reissue No. 28,341), ZSM-3 (U.S. Pat. No. 3,415,736), ZSM-4 (U.S. Pat. No. 4,021,947), ZSM-5 (U.S. Pat. Nos. 3,702,886, 4,797,267 and 5,783,321), ZSM-11 (U.S. Pat. No. 3,709,979), ZSM-12 (U.S. Pat. No. 3,832,449), ZSM-12 and ZSM-38 (U.S. Pat. No. 3,948,758), ZSM-14 (U.S. Pat. No. 3,923,636), ZSM-18 (U.S. Pat. No. 3,950,496), ZSM-20 (U.S. Pat. No. 3,972,983), ZSM-22 (U.S. Pat. No. 5,336,478), ZSM-23 (U.S. Pat. No. 4,076,842), ZSM-34 (U.S. Pat. No. 4,086,186), ZSM-35 (U.S. Pat. No. 4,016,245), ZSM-38, ZSM-48 (U.S. Pat. No. 4,397,827), ZSM-50, ZSM-58 (U.S. Pat. No. 4,698,217), MCM-1 (U.S. Pat. No. 4,639,358), MCM-2 (U.S. Pat. No. 4,673,559), MCM-3 (U.S. Pat. No. 4,632,811), MCM-4 (U.S. Pat. No. 4,664,897), MCM-5 (U.S. Pat. No. 4,639,357), MCM-9 (U.S. Pat. No. 4,880,611), MCM-10 (U.S. Pat. No. 4,623,527), MCM-14 (U.S. Pat. No. 4,619,818), MCM-22 (U.S. Pat. No. 4,954,325), MCM-41 (U.S. Pat. No. 5,098,684), M-41S (U.S. Pat. No. 5,102,643), MCM-48 (U.S. Pat. No. 5,198,203), MCM-49 (U.S. Pat. No. 5,236,575), MCM-56 (U.S. Pat. No. 5,362,697), ALPO-11 (U.S. Pat. No. 4,310,440), ultrastable Y zeolite (USY) (U.S. Pat. Nos. 3,293,192 and 3,449,070), Dealuminized Y zeolite (Deal Y) (U.S. Pat. No. 3,442,795), mordenite (naturally occurring and synthetic) (for synthetic mordenite U.S. Pat. Nos. 3,766,093 and 3,894,104), SSZ-13, titanium aluminosilicates (TASOs) such as TASO-45 (European Patent No. EP-A-0 229 295), boron silicates (U.S. Pat. No. 4,254,297), titanium aluminophosphates (TAPOs) (U.S. Pat. No. 4,500,651), mixtures of ZSM-5 and ZSM-11 (U.S. Pat. No. 4,229,424), ECR-18 (U.S. Pat. No. 5,278,345), SAPO-34 bound ALPO-5 (U.S. Pat. No. 5,972,203), those disclosed in International Publication No. WO 98/57743 published Dec. 23, 1988 (molecular sieve and Fischer-Tropsch), those disclosed in U.S. Pat. No. 6,300,535 (MFI-bound zeolites), mesoporous molecular sieves (U.S. Pat. Nos. 6,284,696, 5,098,684, 5,102,643 and 5,108,725), and the like, and intergrowths and/or combinations thereof.

In an embodiment, the methylation catalyst comprises an aluminosilicate catalyst composition. Aluminosilicates, as used herein, can include those having a molar relationship of $X_2O_3:(n)YO_2$ (wherein X is a trivalent element, e.g., Al; and Y is a tetravalent element, e.g., Si), in which n≤500, such as ≤250, ≤100, such as from 30 to 100.

Non-limiting examples of trivalent X can include aluminum, boron, iron, indium, gallium, and combinations thereof, for example X can be aluminum. Non-limiting examples of tetravalent Y can include silicon, tin, titanium, germanium, and combinations thereof, for example Y can be silicon.

Other non-limiting examples of aluminosilicate catalysts and compositions can be found, for instance, in U.S. Patent Application Publication No. 2003/0176751 and U.S. patent application Ser. No. 11/017,286 (filed Dec. 20, 2004) and 60/731,846 (filed Oct. 31, 2005).

One class of molecular sieve suitable for use in a process of this disclosure has a Constraint Index ≤5, and is crystalline microporous material of the MWW framework type. In at least one embodiment, the crystalline microporous material is a zeolite. As used herein, the term "crystalline microporous material of the MWW framework type" includes one or more of:

(a) molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, incorporated herein by reference);

(b) molecular sieves made from a second degree building block, being a 2-dimensional tiling of such MWW framework topology unit cells, forming a monolayer of one unit cell thickness, in an embodiment, one c-unit cell thickness;

(c) molecular sieves made from common second degree building blocks, being layers of one or more than one unit cell thickness, where the layer of more than one unit cell thickness is made from stacking, packing, or binding at least two monolayers of MWW framework topology unit cells. The stacking of such second degree building blocks can be in a regular fashion, an irregular fashion, a random fashion, or any combination thereof; and (d) molecular sieves made by any regular or random 2-dimensional or 3-dimensional combination of unit cells having the MWW framework topology.

Crystalline microporous materials of the MWW framework type include those molecular sieves having an X-ray diffraction pattern comprising d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system.

Examples of crystalline microporous materials of the MWW framework type include MCM-22 (U.S. Pat. No. 4,954,325), PSH-3 (U.S. Pat. No. 4,439,409), SSZ-25 (U.S. Pat. No. 4,826,667), ERB-1 (European Patent No. 0293032), ITQ-1 (U.S. Pat. No. 6,077,498), ITQ-2 (International Publication No. WO97/17290), MCM-36 (U.S. Pat. No. 5,250, 277), MCM-49 (U.S. Pat. No. 5,236,575), MCM-56 (U.S. Pat. No. 5,362,697), UZM-8 (U.S. Pat. No. 6,756,030), UZM-8HS (U.S. Pat. No. 7,713,513), UZM-37 (U.S. Pat. No. 7,982,084), EMM-10 (U.S. Pat. No. 7,842,277), EMM-12 (U.S. Pat. No. 8,704,025), EMM-13 (U.S. Pat. No. 8,704,023), UCB-3 (U.S. Pat. No. 9,790,143B2) and mixtures thereof.

In some embodiments, the crystalline microporous material of the MWW framework type may be contaminated with other crystalline materials, such as ferrierite or quartz. These contaminants may be present in quantities of ≤10 wt %, such as ≤5 wt %.

In some embodiments, the molecular sieves are not subjected to pre-treatments, such as high temperature steaming, to modify their diffusion properties. In other embodiments, the molecular sieves may be selectivated, either before introduction into the aromatization reactor or in-situ in the reactor, by contacting the catalyst with a selectivating agent, such as silicon, steam, coke, or a combination thereof. In one embodiment, the catalyst is silica-selectivated by contacting the catalyst with at least one organosilicon in a liquid carrier and subsequently calcining the silicon-containing catalyst in an oxygen-containing atmosphere, e.g., air, at a temperature of 350° C. to 550° C. A suitable silica-selectivation procedure is described in U.S. Pat. No. 5,476,823. In another embodiment, the catalyst is selectivated by contacting the catalyst with steam. Steaming of the zeolite is effected at a temperature of ≥950° C., such as from 950° C. to 1075° C., or from 1000° C. to 1050° C., for 10 minutes to 10 hours, such as from 30 minutes to 5 hours. The selectivation procedure, which may be repeated multiple times, alters the diffusion characteristics of the molecular sieve and may increase the xylene yield.

In addition to, or in place of, silica or steam selectivation, the catalyst may be subjected to coke selectivation. This optional coke selectivation typically involves contacting the catalyst with a thermally decomposable organic compound at an elevated temperature in excess of the decomposition temperature of said compound but below the temperature at which the crystallinity of the molecular sieve is adversely affected. Further details regarding coke selectivation techniques are provided in the U.S. Pat. No. 4,117,026. In some embodiments, a combination of silica selectivation and coke selectivation may be employed.

It may be desirable to combine the molecular sieve, prior to selectivating, with at least one oxide modifier, such as at least one oxide selected from elements of Groups 2 to 4 and 13 to 16 of the Periodic Table. In some embodiments, the oxide modifier is selected from oxides of boron, magnesium, calcium, lanthanum, and phosphorus. In some cases, the molecular sieve may be combined with more than one oxide modifier, for example a combination of oxides of phosphorus with calcium and/or magnesium, since in this way it may be possible to reduce the steaming severity needed to achieve a target diffusivity value. In some embodiments, the total amount of oxide modifier present in the catalyst, as measured on an elemental basis, may be from 0.05 wt % and 20 wt %, such as from 0.1 wt % to 10 wt %, based on the weight of the final catalyst. Where the modifier comprises phosphorus, incorporation of modifier into the catalyst is conveniently achieved by the methods described in U.S. Pat. Nos. 4,356,338; 5,110,776; 5,231,064; and 5,348,643.

The molecular sieves may be used as the methylation catalyst without any binder or matrix, in a self-bound form. Alternatively, the molecular sieves may be composited with another material which is resistant to the temperatures and other conditions employed in the methylation reaction. Such binder or matrix materials include active and inactive materials and synthetic or naturally occurring zeolites as well as inorganic materials such as clays and/or oxides such as alumina, silica, silica-alumina, zirconia, titania, magnesia or mixtures of these and other oxides. The latter may be either naturally occurring or in the form of gelatinous precipitates or gels comprising mixtures of silica and metal oxides. Clays may also be included with the oxide type binders to modify the mechanical properties of the catalyst or to assist in its manufacture. Use of a material in conjunction with the molecular sieve whether combined therewith or present during its synthesis, which itself is catalytically active may change the conversion and/or selectivity of the catalyst. Inactive materials suitably serve as diluents to control the amount of conversion so that products may be obtained economically and orderly without employing other means for controlling the rate of reaction. These materials may be incorporated into naturally occurring clays, for example, bentonite and kaolin, to improve the crush strength of the catalyst under commercial operating conditions and function as binders or matrices for the catalyst. The relative proportions of molecular sieve and inorganic oxide matrix vary widely, with the sieve content ranging from 1 wt % to 90 wt %, and in some embodiments the composite is prepared in the form of beads, in the range of 2 wt % to 80 wt % of the composite.

Figure 1:
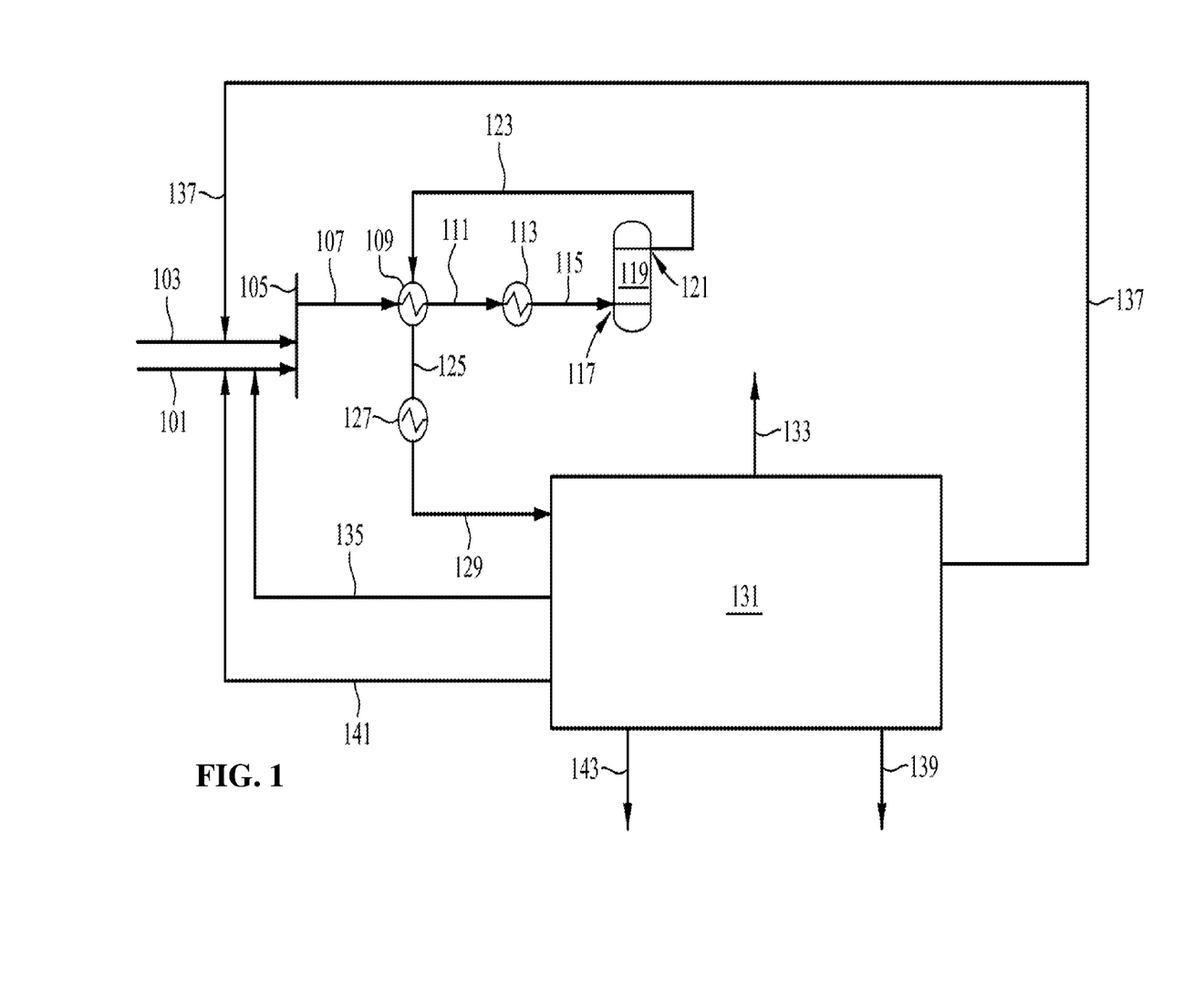
FIG. 1 is a schematic diagram showing a process of this disclosure for converting benzene/toluene via methylation with methanol/dimethyl ether to produce xylenes comprising recycling of DME, methanol, and toluene to the methylation reactor, according to one embodiment of this disclosure.

FIG. 1 schematically illustrates a process for converting benzene and/or toluene via methylation with methanol and/or DME to produce p-xylene according to one embodiment of this disclosure. Methylating agent feed 101, comprising methanol and/or DME is combined with aromatic hydrocarbon feed 103 comprising toluene and/or benzene in fluid transfer line 105. Fluid transfer line 105 may contain an agitator or other mixing device (not shown) in order to combine methylating agent feed 101 and aromatic hydrocarbon feed 103 to form a combined feed. The combined feed is fed by line 107 to heat exchanger 109 to pre-heat the combined feed. The heated combined feed comprising a mixture of feed 101 and feed 103 is fed through line 111 to heat exchanger 113. Heat exchanger 113 may be used to heat or cool the combined feed as necessary. The combined feed is then passed through line 115, through inlet 117 to methylation reactor 119. Line 115 may also include a pump or series of pumps (not shown) in order to maintain sufficient pressure and WHSV in methylation reactor 119. Inlet 117 may accept one or more feeds or streams comprising one or more recycle streams. Methylation reactor 119 can be a fixed or fluid bed reactor containing the methylation catalyst (not shown) and is operated at methylation reaction conditions, which may include a temperature lower than 500° C. and an absolute pressure ≥100 kPa. Methylation reactor 119 may have one or more methylation reactors (not shown) where the methylation catalyst is present. The product of the methylation conditions in the methylation reactor (the methylation product mixture effluent) can be a mixture of xylenes, water, methanol, dimethyl ether, and by-products and is fed from methylation reactor 119 through outlet 121 to line 123 and ultimately to heat exchanger 109 to be cooled. The cooled methylation product mixture effluent is passed through line 125 to heat exchanger 127 to be either heated or cooled as necessary to arrive at the desired temperature for separation, then through line 129 to separation subsystem 131. Separation subsystem 131 may contain one or more separation units (not shown). Separation subsystem 131 may separate methane or other light gases which can be removed via line 133 and may lead be used as fuel gas (not shown).

Separation subsystem 131 may further separate a dimethyl ether-rich stream which is then provided to line 135, which can be recycled into methylating agent feed 101 or methylation reactor inlet 117. Line 135 may include pumps or compressors so that the DME-rich stream may enter the methylation agent feed or methylation reactor at a desired pressure, the combination of lines and pumps or compressors is a first recycling channel. The first recycling channel may contain other combinations of lines and pumps or compressors (not shown) suitable to recycle DME to methylation reactor 119.

Separation subsystem 131 may further separate toluene-rich stream 137, which may contain benzene and can be recycled into aromatic hydrocarbon feed 103 or methylation reactor inlet 117. Line 137 may include pumps or compressors so that the toluene-rich stream may enter the aromatic hydrocarbon feed or methylation reactor at a desired pressure; the combination of lines and pumps or compressors is a second recycling channel. Furthermore, the separation may yield a xylenes-rich stream which is sent out of line 139, and line 139 may be connected to other systems for further processing (not shown). The xylenes-rich stream can be fed to a separation system such as a crystallizer or a simulated moving bed adsorption chromatography to recover a high-purity p-xylene product and produce a p-xylene-depleted stream. The p-xylene-depleted stream can be isomerized in an isomerization reactor in the presence of an isomerization catalyst to produce additional p-xylene.

Separation subsystem 131 may further separate a methanol-rich stream which is then provided to line 141, which can be recycled into methylating agent feed 101 or methylation reactor inlet 117. Line 141 may include pumps or compressors so that the methanol-rich stream may enter the methylation agent feed or methylation reactor at a desired pressure; the combination of lines and pumps or compressors is a third recycling channel. The third recycling channel may contain other combinations of lines and pumps or compressors (not shown) suitable to recycle methanol to methylation reactor 119. Furthermore, the separation may yield a water-rich stream which is sent out of line 143, and line 143 may be connected to other systems for further processing (not shown), comprising wastewater purification systems (not shown).

Figure 2:
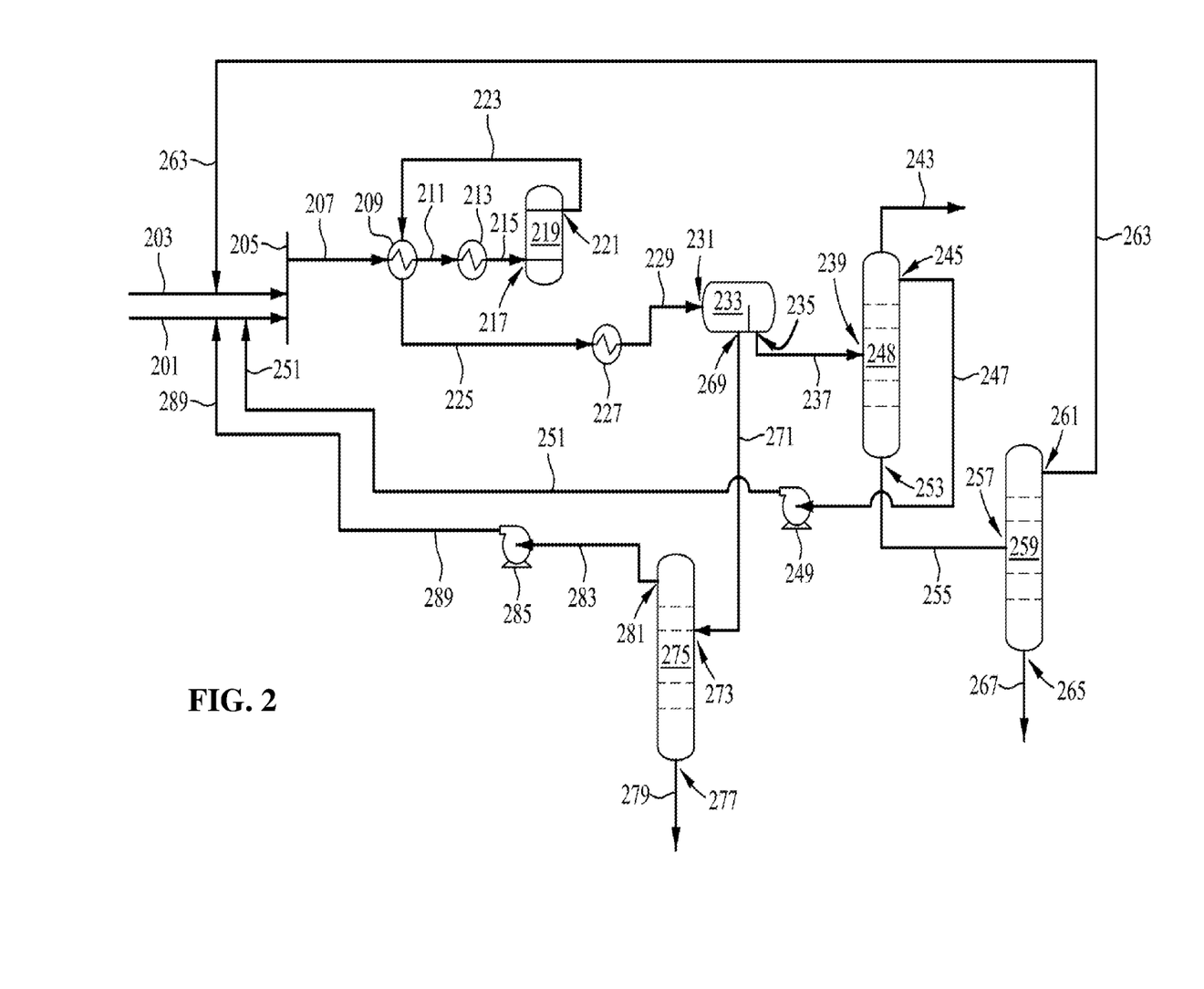
FIG. 2 is a schematic diagram showing a process of this disclosure for converting benzene/toluene via methylation with methanol/dimethyl ether to produce xylenes comprising a separation subsystem including a plurality of separation units which allow for recycling of DME, methanol, and toluene to the methylation reactor, according to one embodiment of this disclosure.

FIG. 2 schematically illustrates a process for converting benzene/toluene via methylation with methanol/dimethyl ether to produce p-xylene according to an embodiment of this disclosure. Methylating agent feed 201, comprising methanol and/or DME, is combined with aromatic hydrocarbon feed 203 comprising toluene and/or benzene in fluid transfer line 205. Fluid transfer line 205 may contain an agitator or other mixing device (not shown) in order to fully combine methylating agent feed 201 and aromatic hydrocarbon feed 203. The combined feed is transferred by line 207 to heat exchanger 209 to pre-heat the combined feed. The heated combined feed comprising a mixture of feed 201 and feed 203 is fed through line 211 to heat exchanger 213. Heat exchanger 213 may be used to heat or cool the combined feed as necessary. The combined feed is then passed through line 215, through inlet 217, to methylation reactor 219. Line 215 may also include a pump or series of pumps (not shown) in order to maintain sufficient pressure and WHSV in methylation reactor 219. Inlet 217 may accept one or more feeds or streams comprising one or more recycle streams. Methylation reactor 219 can be a fixed or fluid bed reactor containing the methylation catalyst (not shown) and is operated at methylation reaction conditions, which may include a temperatures ≤500° C. and pressures ≥100 kPa. Methylation reactor 219 may have one or more methylation reactors (not shown) where the methylation catalyst is present. The product of the methylation conditions in the methylation reactor (the methylation product mixture effluent) can be a mixture of xylenes, water, methanol, dimethyl ether, and by-products. The methylation product mixture effluent is transferred from methylation reactor 219 through outlet 221 to line 223 leading to heat exchanger 209 to be cooled, the cooled methylation product mixture effluent is passed through line 225 to heat exchanger 227 to be either heated or cooled as necessary to arrive at the desired temperature for separation, then through line 229 to inlet 231 of first separation unit 233.

First separation unit 233 separates the aqueous phase (a water/methanol mixture) of the methylation product mixture effluent from the oil phase (a hydrocarbon portion of the methylation product mixture effluent) of the methylation product mixture effluent. First separation unit 233 may function through any suitable method of separating aqueous and oil phases, including simple phase separation, hydrocyclonic separation, or other suitable methods. The oil phase of the methylation product mixture effluent may contain xylenes, methane, dimethyl ether, unreacted benzene or toluene, and other by-products. The hydrocarbon portion of the methylation product mixture effluent is passed through outlet 235 through line 237 to inlet 239 of second separation unit 241. The aqueous phase is passed through outlet 269 to line 271.

Second separation unit 248 separates the oil phase into (i) a light gas portion comprising methane, which can be vented to fuel gas through line 243; (ii) a dimethyl ether-rich stream, which is passed through outlet 245 through line 247 to pump 249, through line 251 and is recycled into methylating agent feed 201 or methylation reactor inlet 217; the combination of lines and pumps or compressors is a first recycling channel; and (iii) a aromatics-rich stream comprising p-xylene, which can be removed for further processing through outlet 253 and line 255. Second separation unit 248 can be a distillation column run at sufficient pressure to allow dimethyl ether to be separated as a liquid while not requiring a bottoms temperature sufficiently high so as to cause decomposition of portions of the methylation product mixture effluent.

The aromatics-rich stream passed though line 255 may be introduced to inlet 257 and into third separation unit 259 where it can be separated. The separation may yield a toluene-rich stream which is sent out of outlet 261 through line 263 and may be recycled to aromatic hydrocarbon feed 203 or methylation reactor inlet 217. Line 263 may include pumps or compressors so that the toluene-rich stream may enter the aromatic hydrocarbon feed or methylation reactor at a desired pressure, the combination of lines and pumps or compressors is a second recycling channel. Furthermore, the separation may yield a xylenes-rich stream which is sent out of outlet 265 through line 267, and line 267 may be connected to other systems for further processing (not shown).

The aqueous phase from first separation unit 233 can be passed through outlet 269 and through line 271 to inlet 273 of fourth separation unit 275. Fourth separation unit 275 separates a water-rich stream and a methanol-rich stream. Fourth separation unit 275 can function through any suitable method of separating methanol and water, including distillation, pervaporation, membrane separation, or other suitable methods. The water rich stream may be passed through outlet 277 and line 279 for further processing or disposal. The methanol rich stream can be sent out of outlet 281 to line 283 and to pump 285. The methanol rich stream may then be passed through line 289 and introduced to methylating agent feed 201 or methylation reactor inlet 217 (not shown). Lines 283 and 289 may contain additional pumps (additional to pump 285) or compressors to return the methanol-rich stream at a desired pressure to either methylation agent feed 201 or methylation reactor inlet 217; the combination of lines and pumps are a third recycle channel.

This disclosure can further include the following non-limiting embodiments:

A1. A process for converting at least one of benzene or toluene, the process comprising: (a) feeding an aromatic hydrocarbon feed and a methylating agent feed into a methylation reactor loaded with a methylation catalyst comprising a zeolite of the MWW framework type, the aromatic hydrocarbon feed comprising at least one of benzene or toluene, and the methylating agent comprising at least one of methanol or dimethyl ether; (b) contacting the aromatic hydrocarbon feed and the methylating agent feed with the methylation catalyst under methylation reaction conditions effective to produce a methylation product mixture effluent comprising toluene, p-xylene, methanol, and dimethyl ether; (c) obtaining a dimethyl ether-rich stream from at least a portion of the methylation product mixture effluent; and (d) recycling at least a portion of the dimethyl ether-rich stream obtained in (c) to (a) as at least a portion of the methylating agent feed.

A2. The process of A1, where in (a), the methylation catalyst is present in the methylation reactor in a fixed bed.

A3. The process of A1 or A2, where in (b), the methylation reaction conditions comprise a temperature in a range from 200 to 500° C., and an absolute pressure in the range from 100 to 8,500 kPa. Optionally, nitrogen, hydrogen, or water can be added to further improve the performance of toluene methylation catalyst.

A4. The process of A3, where in (b), the methylation reaction conditions comprise a temperature in a range from 250 to 400° C.

A5. The process of any of A1 to A4, where in (b), the methylation reaction conditions comprise a weight hourly space velocity of the aromatic hydrocarbon feed in a range from 0.5 to 50 hour$^{-1}$.

A6. The process of A5, where in (b), the methylation reaction conditions comprise a weight hourly space velocity of the aromatic hydrocarbon feed in a range from 5 to 10 hour$^{-1}$.

A7. The process of any of the preceding embodiments, where (c) comprises: (c1) separating the methylation product mixture effluent to obtain an aqueous phase and an oil phase; (c2) separating the oil phase to obtain the dimethyl ether-rich stream of (c) and an aromatics-rich stream comprising p-xylene and toluene.

A8. The process of A7, where (c2) comprises distilling the oil phase in a distillation column at an absolute overhead pressure in a range from 300 to 800 kPa.

A9. The process of A7 or A8, where (c) further comprises: (c3) separating the aromatics-rich stream to obtain a toluene-rich stream and a xylenes-rich stream; and (c4) recycling at least a portion of the toluene-rich stream obtained in (c3) to (a) as at least a portion of the aromatic hydrocarbon feed.

A10. The process of A9, where the toluene-rich stream comprises benzene.

A11. The process of any of A7 to A10, further comprising: (c5) distilling the aqueous phase to obtain a methanol-rich stream and a water-rich stream; and (c6) recycling at least a portion of the methanol-rich stream obtained in (c5) to (a) as at least a portion of the methylating agent feed.

A12. The process of any of the preceding embodiments, where the aromatic hydrocarbon feed comprises at least 90 wt % of toluene, based on the total weight of the aromatic hydrocarbon feed.

A13. The process of any of the preceding embodiments, where the molar ratio of the aromatic hydrocarbon feed to the methylating agent feed is R(a/m), 1≤R(a/m)≤5, and $$R(a/m) = \frac{M(tol) + 2 \cdot M(bz)}{M(\text{methanol}) + 2 \cdot M(DME)},$$

where M(tol) and M(bz) are the moles of toluene and benzene in the aromatic hydrocarbon feed, respectively, and M(methanol) and M(DME) are the moles of methanol and dimethyl ether in the methylating agent feed, respectively.

A14. The process of A13, where 2≤R(a/m)≤4.

A15. The process of any of the preceding embodiments, where the zeolite is selected from MCM-22, PSH-3, SSZ-25, ERB-1, ITQ-1, ITQ-2, MCM-36, MCM-49, MCM-56, EMM-10, EMM-12, EMM-13, UZM-8, UZM-8HS, UZM-37, UCB-3 and mixtures of two or more thereof.

A16. The process of A16, where the zeolite is selected from MCM-22, MCM-49, and mixtures thereof.

B1. A process for converting benzene and/or toluene, the process comprising:

(I) feeding an aromatic hydrocarbon feed and a methylating agent feed into a methylation reactor, wherein the aromatic hydrocarbon feed comprises benzene and/or toluene, and the methylating agent comprises methanol and/or dimethyl ether, wherein the molar ratio of the aromatic hydrocarbon feed to the methylating agent feed is R(a/m), $$R(a/m) = \frac{M(tol) + 2 \cdot M(bz)}{M(\text{methanol}) + 2 \cdot M(DME)},$$

where M(tol) and M(bz) are the moles of toluene and benzene in the aromatic hydrocarbon feed, respectively, and M(methanol) and M(DME) are the moles of methanol and dimethyl ether in the methylating agent feed, respectively, and wherein 1≤R(a/m)≤5;

(II) contacting the aromatic hydrocarbon feed with the methylating agent feed in the presence of a methylation catalyst in the methylation reactor under methylation reaction conditions effective to produce a methylation product mixture effluent exiting the methylation reactor, wherein the methylation catalyst comprises a zeolite, and the methylation product mixture effluent comprise toluene, p-xylene, methanol, and dimethyl ether;

(III) obtaining a dimethyl ether-rich stream from at least a portion of the methylation product mixture effluent; and (IV) recycling at least a portion of the dimethyl ether-rich stream obtained in (c) to (a) as at least a portion of the methylating agent feed.

B2. The process of claim 17, wherein the methylation reaction conditions comprise a weight hourly space velocity based on the total flow rate of the aromatic hydrocarbon feed and the methylating agent feed is in a range from 5 to 10 hour$^{-1}$.

B3. The process of claim 17 or claim 18, wherein 2≤R(a/m)≤4.

B4. The process of any of claims 17 to 19, wherein the zeolite is a MWW framework type zeolite.

B5. The process of any of claims 17 to 20, wherein the methylation catalyst is present in a fixed bed, and the methylation reaction conditions comprise a temperature in a range from 200 to 500° C., and an absolute pressure in the range from 100 to 8,500 kPa.

C1. A system for converting benzene and/or toluene to xylenes, comprising: (I) a methylation reactor adapted for receiving a methylation catalyst comprising a zeolite of the MWW framework type comprising at least one reactor inlet adapted for receiving an aromatic hydrocarbon feed and a methylating agent feed and a reactor outlet adapted for discharging a methylation product mixture effluent comprising xylenes, methanol, and dimethyl ether, the methylation reactor further configured to allow contacting the aromatic hydrocarbon feed and the methylating agent feed with the methylation catalyst under methylation reaction conditions effective to produce the methylation product mixture effluent; and (II) a separation subsystem in fluid communication with the reactor outlet adapted for obtaining from the methylation product mixture effluent a dimethyl ether-rich stream; and (III) a first recycling channel connecting the separation subsystem and the at least one reactor inlet of the methylation reactor, the first recycling channel adapted for recycling at least a portion of the dimethyl ether-rich stream to the methylation reactor.

C2. The system of C1, where the separation subsystem in (II) comprises: (IIa) a first separation unit comprising an inlet for receiving the methylation product mixture effluent, an outlet for discharging an aqueous phase, and an outlet for discharging an oil phase, the separation unit configured to separate the methylation product mixture effluent to the aqueous phase and the oil phase; and (IIb) a second separation unit comprising an inlet for receiving the oil phase, an first outlet for discharging the dimethyl ether-rich stream, and a second outlet for discharging an aromatics-rich stream.

C3. The system of C2, where the second separation unit is a distillation column.

C4. The system of any of C1 to C3, where the separation subsystem further comprises: (IIc) a third separation unit comprising an inlet for receiving the aromatics-rich stream, an first outlet for discharging a toluene-rich stream, and a second outlet for discharging a xylenes-rich stream; and (IId) a second recycling channel connecting the lower outlet in (IIc) and the at least one reactor inlet of the methylation reactor, the second recycling channel adapted for recycling at least a portion of the toluene-rich stream to the methylation reactor.

C5. The system of C4, where the third separation unit is a distillation column.

C6. The system of C1 to C5, where the separation subsystem further comprises: (IIe) a fourth separation unit in fluid communication with the first separation unit, comprising an inlet for receiving the aqueous phase, an first outlet for discharging a methanol-rich stream, and a second outlet for discharging a water-rich stream; and (IIf) a third recycling channel connecting the fourth separation unit and the at least one inlet of the methylation reactor, the third recycling channel configured to recycle at least a portion of the methanol-rich stream to the methylation reactor.

C7. The system of any of C1 to C6, further comprising a xylenes-loop comprising an inlet for receiving the xylenes-rich stream from the third separation unit, and a p-xylene recovery unit, optionally an o-xylene recovery unit, and a xylenes isomerization unit.

EXAMPLES

Figure 3:
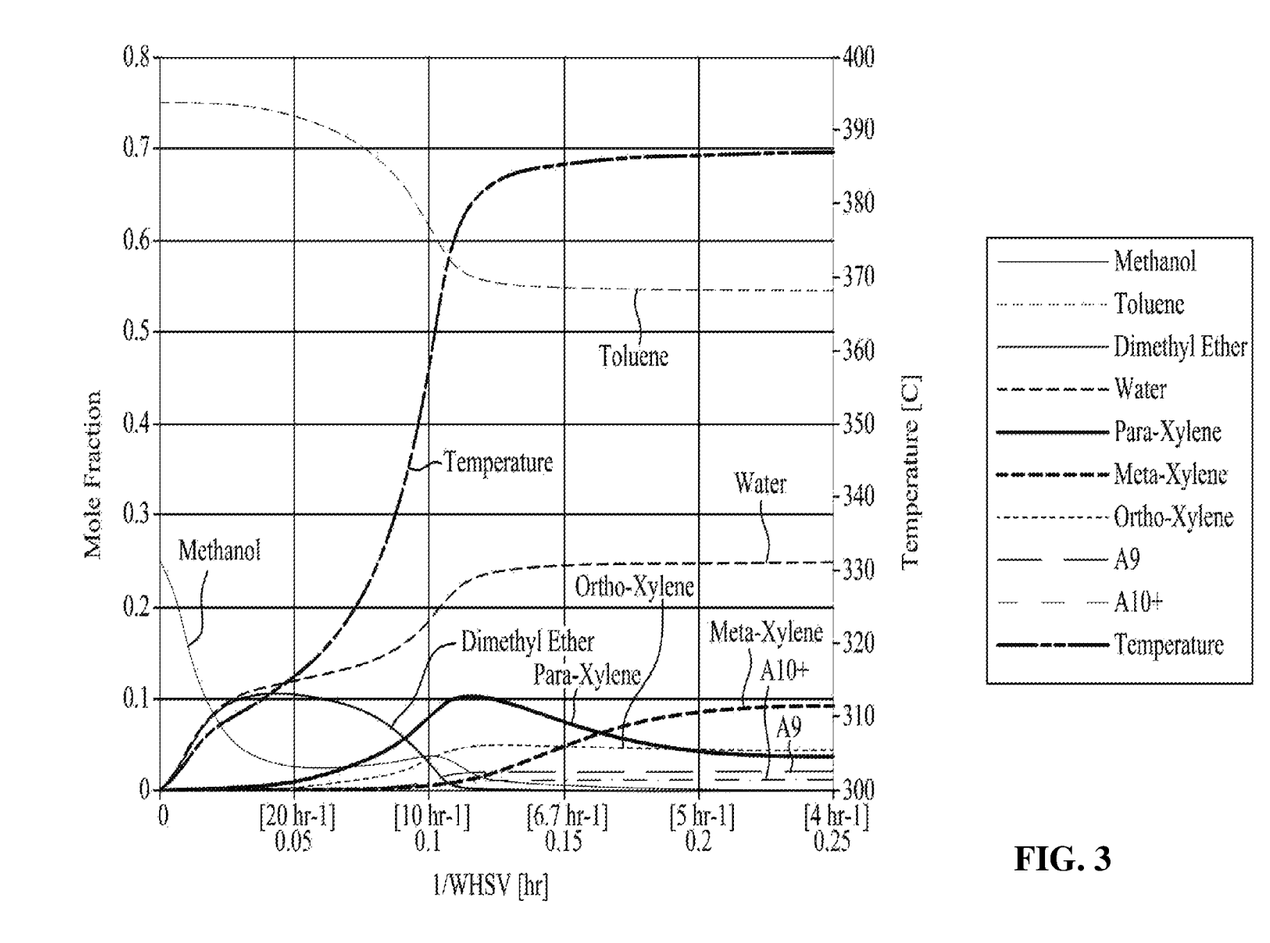
FIG. 3 is a graph showing reaction temperature and mole fractions of reactants and various products as a function of the reciprocal of weight hourly space velocity of toluene and methanol feeds in an exemplary process for converting benzene/toluene via methylation with methanol, according to one embodiment of this disclosure.

An exemplary process for converting toluene via methylation with methanol in the presence of a catalyst to produce xylenes in an adiabatic reactor was simulated. Only toluene and methanol (at a toluene to methanol molar ratio of 3) is fed into the reactor with no recycling. In FIG. 3, mole fractions of the reactants and the products and temperature of the simulated process are shown on the y-axis, and the reciprocal of weight hourly space velocity on the x-axis. The data demonstrate three distinct reactive waves. First, methanol enters the methylation reactor (methylation reactor) and is converted to and comes to equilibrium with dimethyl ether (DME). Then the concentration of methanol and DME declines as the toluene is methylated. The initial species formed are the para and ortho isomers of the xylenes, with the para isomer heavily favored. Eventually the concentration of the para isomer declines as isomerization to the meta isomer occurs. If the reactor is large enough and the reaction allowed to proceed, substantially most or all the methanol and dimethyl ether will be used and the various isomers will isomerize to equilibrium concentrations. From FIG. 3, it can be seen that at a weight hourly space velocity in the range from 6.7 to 10 hr-1, the methylation reaction product mixture effluent tends to comprise p-xylene at peak concentration that is significantly higher than o-xylene and m-xylene concentrations, and also significantly higher than the equilibrium concentration of p-xylene. Thus, it would be highly desirable to run the methylation process in this space velocity range to maximize the production of p-xylene. In this space velocity range, the methylation reaction product mixture effluent can comprise methanol and possibly dimethyl ether. Therefore, separation and recycling of methanol and possibly dimethyl ether may be advantageous.

Overall, processes of this disclosure can be performed at a limited space time (i.e., the reciprocal of weight hourly space velocity of the aromatic hydrocarbon feed and the methylating agent feed combined) and a temperature ≤500° C., which provides benzene and/or toluene methylation with methanol and/or dimethyl ether to produce p-xylene with higher selectivity, less light gas by-products, and longer catalyst cycle life as compared to conventional toluene/benzene methylation processes. Also, processes of this disclosure can be performed at increased pressure in a methylation reactor which can lead to higher p-xylene selectivity. Peak p-xylene selectivity occurs at lower methanol utilization and therefore a higher WHSV, which is more selective to the p-xylene isomer. The partial consumption of methanol leaves unreacted methanol and DME in the methylation product mixture effluent which can be separated and recycled to the methylation reactor in order to selectively produce higher yields of p-xylene with lower energy consumption, as compared to conventional toluene/benzene methylation processes. Furthermore methanol can be recovered by first separating an aqueous phase from the methylation product stream and then removing the methanol from the aqueous phase. DME can be recovered from the oil phase of the methylation product mixture effluent by distillation. At certain distillation pressures DME may be condensed without the need for cryogenic temperatures in the overhead of the distillation unit.

The phrases, unless otherwise specified, "consists essentially of" and "consisting essentially of" do not exclude the presence of other steps, elements, or materials, whether or not, specifically mentioned in this specification, so long as such steps, elements, or materials, do not affect the basic and novel characteristics of this disclosure, additionally, they do not exclude impurities and variances normally associated with the elements and materials used.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, within a range includes every point or individual value between its end points even though not explicitly recited. Thus, every point or individual value may serve as its own lower or upper limit combined with any other point or individual value or any other lower or upper limit, to recite a range not explicitly recited.

All documents described herein are incorporated by reference herein, including any priority documents and/or testing procedures to the extent they are not inconsistent with this text. As is apparent from the foregoing general description and the specific embodiments, while forms of this disclosure have been illustrated and described, various modifications can be made without departing from the spirit and scope of this disclosure. Accordingly, it is not intended that this disclosure be limited thereby. Likewise, the term "comprising" is considered synonymous with the term "including" for purposes of United States law. Likewise whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

While this disclosure has been described with respect to a number of embodiments and examples, those skilled in the art, having benefit of this disclosure, will appreciate that other embodiments can be devised which do not depart from the scope and spirit of this disclosure.

What is claimed is:

1. A process for converting benzene and/or toluene, the process comprising:
   (a) feeding an aromatic hydrocarbon feed and a methylating agent feed into a methylation reactor, wherein the aromatic hydrocarbon feed comprises benzene and/or toluene, and the methylating agent feed comprises methanol and/or dimethyl ether;
   (b) contacting the aromatic hydrocarbon feed with the methylating agent feed in the presence of a methylation catalyst in the methylation reactor under methylation reaction conditions effective to produce a methylation product mixture effluent exiting the methylation reactor, wherein the methylation catalyst comprises a zeolite of the MWW framework type, and the methylation product mixture effluent comprises toluene, p-xylene, methanol, and dimethyl ether;
   (c) Obtaining a dimethyl ether-rich stream from at least a portion of the methylation product mixture effluent, wherein (c) comprises:
      (c1) separating the methylation product mixture effluent to obtain an aqueous phase and an oil phase; and
      (c2) separating the oil phase to obtain the dimethyl ether-rich stream of (c) and an aromatics-rich stream comprising p-xylene and toluene; and
   (d) recycling at least a portion of the dimethyl ether-rich stream Obtained in (c) to (a) as at least a portion of the methylating agent feed.

2. The process of claim 1, wherein in (b), the methylation reaction conditions comprise a temperature in a range from 200 to less than 500° C., and an absolute pressure in the range from 100 to 8,500 kPa.

3. The process of claim 1, wherein the molar ratio of the aromatic hydrocarbon feed to the methylating agent feed is R(a/m), $$R(a/m) = \frac{M(tol) + 2 \cdot M(bz)}{M(\text{methanol}) + 2 \cdot M(DME)},$$

where M(tol) and M(bz) are the moles of toluene and benzene in the aromatic hydrocarbon feed, respectively, and M(methanol) and M(DME) are the moles of methanol and dimethyl ether in the methylating agent feed, respectively, and wherein $1 \leq R(a/m) \leq 5$.

4. The process of claim 1, wherein in (b), the methylation reaction conditions comprise a weight hourly space velocity based on the total flow rate of the aromatic hydrocarbon feed and the methylating agent feed in a range from >10 hour$^{-1}$ to 50 hour$^{-1}$.

5. The process of claim 1, wherein (c) further comprises:
   (c3) separating the aromatics-rich stream to obtain a toluene-rich stream and a xylenes-rich stream; and
   (c4) recycling at least a portion of the toluene-rich stream obtained in (c3) to (a) as at least a portion of the aromatic hydrocarbon feed.

6. The process of claim 1, further comprising:
   (c5) distilling the aqueous phase to obtain a methanol-rich stream and a water-rich stream; and
   (c6) recycling at least a portion of the methanol-rich stream Obtained in (c5) to (a) as at least a portion of the methylating agent teed.

7. The process of claim 1, wherein the aromatic hydrocarbon feed comprises at least 90 wt % of toluene, based on the total weight of the aromatic hydrocarbon feed.

8. The process of claim 1, wherein the zeolite is selected from MCM-22, PSH-3, SSZ-25, ERB-1, ITQ-1, ITQ-2, MCM-36, MCM-49, MCM-56, EMM-10, EMM-12, EMM-13, UZM-8HS, UZM-37, UCB-3, and mixtures of two or more thereof.

9. The process of claim 8, wherein the zeolite is selected from MCM-22, MCM-49, comprises MCM-56, and mixtures thereof.

10. The process of claim 1, wherein:
    the methylation product mixture effluent further comprises o-xylene and m-xylene,
    a ratio of the p-xylene to the m-xylene is greater than 5:1, and
    a ratio of the o-xylene to the m-xylene is greater than 3:1.

11. The process of claim 10, wherein the ratio of the p-xylene to the m-xylene is greater than 7:1, and wherein the ratio of the o-xylene to the m-xylene is greater than 4:1.

12. The process of claim 10, wherein:
    the ratio of the p-xylene to the m-xylene is greater than 7:1,
    a ratio of a combined amount of the p-xylene and the o-xylene to the m-xylene is >10:1, and
    the methylation product mixture effluent comprises <10 wt % of the m-xylene, based on the total weight of all xylenes in the methylation product mixture effluent.

13. The process of claim 1, wherein in (h), the methylation reaction conditions comprise a weight hourly space velocity based on the total flow rate of the aromatic hydrocarbon feed and the methylating agent feed in a range from 6.7 hour$^{-1}$ to 10 hour$^{-1}$.

14. The process of claim 1, wherein (c2) is carried out in a distillation column and the dimethyl ether-rich stream comprises ≥50 wt % of dimethyl ether, based on the total weight of the dimethyl ether-rich stream.

15. The process of claim 1, wherein the methylation reaction conditions comprise a temperature in a range from 200 to less than 450° C.

16. The process of claim 1, wherein the methylation reaction conditions comprise a temperature in a range from greater than 400 to less than 500° C.

17. The process of claim 1, wherein:
the aromatic hydrocarbon feed comprises toluene,
the methylating agent feed comprises methanol, and
the methylation reaction conditions comprise a temperature in a range from 200 to less than 500° C. and a weight hourly space velocity based on the total flow rate of the aromatic hydrocarbon feed and the methylating agent feed in a range from 6.7 hour$^{-1}$ to 10 hour$^{-1}$.

18. The process of claim 1, wherein:
the aromatic hydrocarbon feed comprises toluene,
the methylating agent feed comprises methanol, and
the methylation reaction conditions comprise a temperature in a range from 275 to less than 400° C. and a weight hourly space velocity based on the total flow rate of the aromatic hydrocarbon feed and the methylating agent feed in a range from 6.7 hour$^{-1}$ to 10 hour$^{-1}$.

19. The process of claim 18, wherein:
the methylation product mixture effluent further comprises o-xylene and m-xylene,
a ratio of the p-xylene to the m-xylene is greater than 5:1, and
a ratio of the o-xylene to the m-xylene is greater than 3:1.

20. A process for converting benzene and/or toluene, the process comprising:
(I) feeding an aromatic hydrocarbon feed and a methylating agent feed into a methylation reactor, wherein the aromatic hydrocarbon feed comprises benzene and/or toluene, and the methylating agent comprises methanol and/or dimethyl ether, wherein the molar ratio of the aromatic hydrocarbon feed to the methylating agent feed is R(a/m), $$R(a/m) = \frac{M(tol) + 2 \cdot M(bz)}{M(\text{methanol}) + 2 \cdot M(DME)},$$

where M(tol) and M(hz) are the moles of toluene and benzene in the aromatic hydrocarbon feed, respectively, and M(methanol) and M(DME) are the moles of methanol and dimethyl ether in the methylating agent feed, respectively, and wherein 1≤R(a/m)≤5;
(II) contacting the aromatic hydrocarbon feed with the methylating agent feed in the presence of a methylation catalyst in the methylation reactor under methylation reaction conditions effective to produce a methylation product mixture effluent exiting the methylation reactor, wherein the methylation catalyst comprises a zeolite, and the methylation product mixture effluent comprises toluene, p-xylene, methanol, and dimethyl ether;
(III) obtaining a dimethyl ether-rich stream from at least a portion of the methylation product mixture effluent, wherein (III) comprises:
(IIIa) separating the methylation product mixture effluent to obtain an aqueous phase and an oil phase; and
(IIIb) separating the oil phase to obtain the dimethyl ether-rich stream of (III) and an aromatics-rich stream comprising p-xylene and toluene; and
(IV) recycling at least a portion of the dimethyl ether-rich stream obtained in (IIIb) to (I) as at least a portion of the methylating agent feed.

21. The process of claim 17, wherein the zeolite is a MWW framework type zeolite, and wherein the methylation reaction conditions comprise a weight hourly space velocity based on the total flow rate of the aromatic hydrocarbon feed and the methylating agent feed is in a range from 5 to 10 hour$^{-1}$.

22. The process of claim 20, wherein the methylation catalyst is present in a fixed bed, and the methylation reaction conditions comprise a temperature in a range from 200 to less than 500° C., and an absolute pressure in the range from 100 to 8,500 kPa.

23. The process of claim 20, wherein:
the methylation product mixture effluent further comprises o-xylene and m-xylene,
a ratio of the p-xylene to the m-xylene is greater than 5:1, and
a ratio of the o-xylene to the m-xylene is greater than 3:1.

24. A system for converting benzene and/or toluene to xylenes, comprising:
(I) a methylation reactor adapted for receiving a methylation catalyst comprising a zeolite of the MWW framework type comprising at least one reactor inlet adapted for receiving an aromatic hydrocarbon feed and a methylating agent feed and a reactor outlet adapted for discharging a methylation product mixture effluent comprising xylenes, methanol, and dimethyl ether, the methylation reactor further configured to allow contacting the aromatic hydrocarbon feed and the methylating agent feed with the methylation catalyst under methylation reaction conditions effective to produce the methylation product mixture effluent;
(II) a separation subsystem in fluid communication with the reactor outlet adapted for obtaining from the methylation product mixture effluent a dimethyl ether-rich stream, wherein the separation subsystem comprises:
(IIa) a first separation unit comprising an inlet for receiving the methylation product mixture effluent, an outlet for discharging an aqueous phase, and an outlet for discharging an oil phase, the first separation unit configured to separate the methylation product mixture effluent into the aqueous phase and the oil phase; and
(IIb) a second separation unit comprising a distillation column having an inlet for receiving the oil phase, a first outlet for discharging the dimethyl ether-rich stream, and a second outlet for discharging an aromatics-rich stream; and
(III) a first recycling channel connecting the first outlet of the distillation column and the at least one reactor inlet of the methylation reactor, the first recycling channel adapted for recycling at least a portion of the dimethyl ether-rich stream to the methylation reactor.

25. The system of claim 24, wherein the separation subsystem further comprises:
(IIc) a third separation unit comprising an inlet for receiving the aromatics-rich stream, a first outlet for discharging a toluene-rich stream, and a second outlet for discharging a xylenes-rich stream; and
(IId) a second recycling channel connecting the first outlet in (IIc) and the at least one reactor inlet of the methylation reactor, the second recycling channel adapted for recycling at least a portion of the toluene-rich stream to the methylation reactor.

26. The system of claim 25, wherein the separation subsystem further comprises:
- (IIe) a fourth separation unit in fluid communication with the first separation unit, comprising an inlet for receiving the aqueous phase, a first outlet for discharging a methanol-rich stream, and a second outlet for discharging a water-rich stream; and
- (IIf) a third recycling channel connecting the fourth separation unit and the at least one inlet of the methylation reactor, the third recycling channel configured to recycle at least a portion of the methanol-rich stream to the methylation reactor.

\* \* \* \* \*